(12) United States Patent
Riskin et al.

(10) Patent No.: US 11,710,574 B2
(45) Date of Patent: Jul. 25, 2023

(54) HIGH VALIDITY REAL-WORLD EVIDENCE STUDY WITH DEEP PHENOTYPING

(71) Applicant: Verantos, Inc., Menlo Park, CA (US)

(72) Inventors: Daniel Riskin, Menlo Park, CA (US); Anand Shroff, San Carlos, CA (US)

(73) Assignee: Verantos, Inc., Menlo Park, CA (US)

( * ) Notice: Subject to any disclaimer, the term of this patent is extended or adjusted under 35 U.S.C. 154(b) by 0 days.

(21) Appl. No.: 17/581,403

(22) Filed: Jan. 21, 2022

(65) Prior Publication Data

US 2022/0238237 A1 Jul. 28, 2022

Related U.S. Application Data

(60) Provisional application No. 63/142,432, filed on Jan. 27, 2021.

(51) Int. Cl.
*G16H 50/70* (2018.01)
*G06F 40/30* (2020.01)
*G16H 10/60* (2018.01)

(52) U.S. Cl.
CPC ............ *G16H 50/70* (2018.01); *G06F 40/30* (2020.01); *G16H 10/60* (2018.01)

(58) Field of Classification Search
CPC ......... G16H 50/70; G16H 10/60; G06F 40/30
See application file for complete search history.

(56) References Cited

U.S. PATENT DOCUMENTS

| | | | |
|---|---|---|---|
| 7,028,038 B1 | 4/2006 | Pakhomov | |
| 9,015,031 B2 | 4/2015 | Ferrucci | |
| 9,213,687 B2 | 12/2015 | Au | |
| 9,959,328 B2 | 5/2018 | Jain et al. | |
| 10,592,505 B2 | 3/2020 | Galitsky | |
| 10,679,008 B2 | 6/2020 | Dubey et al. | |
| 2003/0135095 A1 | 7/2003 | Iliff | |
| 2005/0033569 A1 | 2/2005 | Yu | |

(Continued)

FOREIGN PATENT DOCUMENTS

| | | |
|---|---|---|
| WO | 2020201078 A1 | 10/2020 |
| WO | 2020222005 A1 | 11/2020 |

OTHER PUBLICATIONS

McInnes et al., "Knowledge-based methods for determining the meaning of ambiguobiomedical terms using information content measures of similarity", in AMIA Annual Symposium Proceedings, vol. 2011, pp. 895-904, Oct. 24, 2011, [retrieved on Mar. 21, 2022] from the internet: <https://www.ncbi.nlm.nih.gov/pmc/articles/PMC3243213/pdf/0895amia2011_proc.pdf>.

(Continued)

*Primary Examiner* — Maroun P Kanaan (57) ABSTRACT

Systems and methods are described for implementing an advanced, "research-grade" or "regulatory-grade," real-world evidence (RWE) approach. The advanced RWE is able to extract a deep phenotype from rich data sources using advanced technologies including artificial intelligence. The rich data sources include both unstructured data and structured data from electric health records and may include additional data sources such as claims or registries. Systems and methods are also described for validating the deep phenotype which can then be used to create a patient cohort that may be linked to exposure or outcome data to make credible clinical assertions.

14 Claims, 4 Drawing Sheets

(56) References Cited

U.S. PATENT DOCUMENTS

| | | |
|---|---|---|
| 2005/0080613 A1 | 4/2005 | Colledge et al. |
| 2007/0116036 A1 | 5/2007 | Moore |
| 2008/0109454 A1 | 5/2008 | Willse et al. |
| 2008/0306872 A1 | 12/2008 | Felsher |
| 2009/0006359 A1 | 1/2009 | Liao |
| 2009/0259629 A1 | 10/2009 | Wei et al. |
| 2012/0084076 A1 | 4/2012 | Boguraev et al. |
| 2013/0110500 A1 | 5/2013 | Feng et al. |
| 2013/0226616 A1 | 8/2013 | Nigam et al. |
| 2015/0193583 A1 | 7/2015 | McNair et al. |
| 2017/0017635 A1 | 1/2017 | Leliwa et al. |
| 2017/0109438 A1 | 4/2017 | Oliver |
| 2017/0199963 A1 | 7/2017 | Kondadadi et al. |
| 2017/0213222 A1 | 7/2017 | Rajpathak et al. |
| 2019/0006027 A1* | 1/2019 | Sacaleanu .............. G16H 50/30 |
| 2019/0156923 A1 | 5/2019 | Kain et al. |
| 2020/0043612 A1 | 2/2020 | McNair et al. |
| 2020/0073996 A1 | 3/2020 | Wright et al. |
| 2020/0104360 A1 | 4/2020 | Gahlot et al. |
| 2020/0402625 A1 | 12/2020 | Aravamudan et al. |
| 2021/0090694 A1* | 3/2021 | Colley ................... G16B 40/00 |
| 2022/0068493 A1 | 3/2022 | Potter et al. |

OTHER PUBLICATIONS

Navigli, "Word Sense Disambiguation: A Survey," ACM Computing Surveys (CSUR), 41(2), pp. 10:1-10:69, Feb. 17, 2009, [retrieved from the internet on Mar. 21, 2022] <http://citeseerx.isl.psu.edu/viewdoc/download?doi=10.1.1.153.8457&rep=rep1&type=pdf>.

Stevenson et al., "Disambiguation of ambiguous biomedical terms using examples generated from the UMLS Metathesaurus", Journal of Biomedical Informatics, vol. 43, pp. 762-773. San Diego, USA.

* cited by examiner

HIGH VALIDITY REAL-WORLD EVIDENCE STUDY WITH DEEP PHENOTYPING

CROSS-REFERENCE TO RELATED APPLICATIONS

This application is claims the benefit under 35 U.S.C. § 119(e) of U.S. Application No. 63/142,432, filed Jan. 27, 2021, the contents of which are incorporated by reference in their entirety.

BACKGROUND

There is a national desire in the United States to implement real-world evidence (RWE) within regulatory, reimbursement, and clinical pathways as a step toward personalized medicine, improved care, and more efficient care. This will accelerate use of routinely collected data to refine care. By influencing what is approved, reimbursed, and selected for care, RWE will adjust the standard of care.

Adjusting the standard of care, however, can have unintended and dangerous consequences. Inaccurate data allowed into a patient's electronic health record (EHR) has the potential to hurt one patient. Inaccurate data allowed into regulatory or reimbursement pathways can harm an entire nation.

RWE is often used to support trial recruitment, trial design, and marketing insight. As it is increasingly used to make clinical assertions, there is reason to believe that current approaches may benefit from greater rigor. Claims data often have accuracy below 50% (see, e.g., Jollis et al., Ann Intern Med. 1993; 119(8):844-50 and Lawson et al., Ann Surg. 2012; 256(6):973-81). Likewise, EHR problem lists often have accuracy below 60% (see, e.g., Luna et al., Stud Health Technol Inform. 2013; 192:417-21, Wright et al., Int J Med Inform. 2015; 84(10):784-90, Onofrei et al., Inform Prim Care. 2004; 12(3):139-45, and Parsons et al., J Am Med Inform Assoc. 2012; 19(4):604-9). In particular, the low accuracy can be attributed to low sensitivity. Low sensitivity may incorporate bias since sicker patients with more touch points in the health system have more complete documentation. Incomplete data that lead to biased patient selection in a study can lead to incorrect clinical assertions.

There is, therefore, a need for new and more rigorous approaches to RWE. Further, such a need is urgent as regulators, payers, and providers are increasingly incorporating RWE insights into their decision-making processes.

SUMMARY

The present technology provides innovations in phenotyping, reference standards, accuracy measurement, and enhanced privacy and security. With such innovations, a deep phenotype can be extracted from rich data sources. The deep phenotype can be validated and then used to create a patient cohort that may be linked to exposure or outcome data to make credible clinical assertions. Built upon such a deep phenotype, the advanced RWE technology of the present disclosure can be recognized as "research-grade" or "regulatory-grade."

In accordance with one embodiment of the present disclosure, provided is a method for defining a real-world evidence (RWE)-based cohort, comprising extracting, from unstructured data (optionally along with structured data) in an electronic health record (EHR), e.g., using a semantic processing technique, a plurality of clinical concepts (optionally with concept attributes) associated with patients; mapping each of the extracted clinical concepts to a coded clinical concept; and comparing the mapped clinical concepts to pre-defined inclusion or exclusion criteria to define a cohort of the patients within the EHR that satisfy a desired phenotype.

In some embodiments, the methods may further comprise generating a RWE-based registry for the cohort that comprises phenotypes associated with at least a subset of the cohort. In some embodiments, the methods may further comprise conducting a trial recruitment of at least a subset of the cohort to enroll in a consented study. In some embodiments, the methods may further comprise conducting a trial recruitment of at least a subset of the cohort to enroll in a randomized controlled trial (RCT). In some embodiments, the methods may further comprise conducting a trial recruitment of at least a subset of the cohort to enroll in a pragmatic control trial (PCT).

Another embodiment provides a method for defining a real-world evidence (RWE)-based cohort, comprising extracting, from unstructured data (optionally along with structured data) in an electronic health record (EHR), e.g., using a semantic processing technique, a plurality of clinical concepts (optionally with concept attributes) associated with patients; mapping each of the extracted clinical concepts to a coded clinical concept; and comparing the mapped clinical concepts to an analytic model to determine a cohort risk profile. In some embodiments, the method may further comprise using the cohort risk profile within value-based contracting.

Yet another embodiment provides a method for conducting a real-world evidence (RWE) study, comprising extracting, from unstructured data in an electronic health record (EHR), a plurality of clinical concepts relating to phenotypes; identifying a cohort of patients from the EHR with a patient phenotype that satisfies at least a portion of a criteria of a study phenotype; obtaining, for the cohort, exposure data and outcome data relating to at least a portion of the patients within the identified cohort; and implementing a RWE study based on the patient phenotype associated with the exposure data or the outcome data for at least one of the patients.

Still a further embodiment provides a method for generating a real-world evidence (RWE)-based cohort having measured data accuracy, comprising extracting, from unstructured data in an electronic health record (EHR), using a semantic processing technique, a plurality of clinical concepts; mapping each of the extracted clinical concepts to a coded clinical concept; comparing the mapped clinical concepts and concept attributes to pre-defined inclusion or exclusion criteria to define a cohort of the patients within the EHR that satisfy a desired phenotype; creating a manually-generated gold standard for a portion of the clinical concepts within a portion of the patients within the cohort; and measuring an accuracy of the semantic processing extraction of the clinical concepts for the cohort to determine validity of the cohort with respect to the manually-generated gold standard for a subset of the cohort, based on at least a portion of the inclusion or exclusion criteria.

In some embodiments, the methods may further comprise associating at least a subset of the clinical concepts and concept attributes with a desired phenotype, wherein the desired phenotype satisfies a threshold phenotypic similarity to a phenotype in a randomized controlled trial. In some embodiments, the methods may further comprise associating at least a subset of the clinical concepts and concept attributes with a desired phenotype, wherein the desired phenotype satisfies a threshold phenotypic similarity to a phenotype in an existing or anticipated regulatory-approved label.

In some embodiments, the implementing of the RWE study comprises conducting, based on the cohort, an observational study. In some embodiments, the implementing of the RWE study comprises comparing outcomes from the outcome data of the cohort with outcomes from an interventional study so that the cohort functions as a synthetic control arm. In some embodiments, the implementing of the RWE study comprises comparing outcomes of the cohort with outcomes from another cohort or another study to determine comparative effectiveness of at least two treatments. In some embodiments, the implementing of the RWE study comprises implementing the association of the patient phenotype with the exposure data or the outcome data through data linkage with another data set. In some embodiments, the another data set comprises a claims data set or a registry.

DETAILED DESCRIPTION

The present disclosure provides an improved approach to RWE, at least in part rooted in computer technology, that overcomes the previously discussed problems and achieves accuracy sufficient for credible clinical assertions, also known as "research-grade" or "regulatory-grade" RWE.

Without limitation, the improved RWE is built upon the following innovations. First, a novel phenotyping approach is provided which combines structured data with unstructured enriched using artificial intelligence in order to achieve a deep phenotype. Second, the deep phenotype may be used to create a patient cohort which may be linked to exposure or outcome data either within an electronic health record (EHR) or from another data source. Third, a new procedure for assessing data validity is described, which measures data accuracy with accuracy requirements defined within a study protocol. Fourth, integral to the new data validity assessment method is a chart abstraction reference standard with minimum required inter-rater reliability.

I. Real World Evidence (RWE)

United States healthcare is embroiled in a crisis of inconsistent quality and overwhelming cost. Through three administrations, the national healthcare strategy has focused on using data and technology to control costs and improve care.

In the first decade of healthcare data reform, between 2010 and 2020, there was uptake of electronic health records (EHRs) and implementation of population health programs. These achieved more consistent application of care pathways, though they did not change the standard of care.

In the second decade of healthcare data reform, from 2020 to 2030, there is a desire to use routinely collected data to enhance the standard of care. While the randomized controlled trial (RCT) remains the bedrock of clinical science, due to expense and difficult implementation, RCTs cannot provide answers to all questions. Given a set of safe and effective options to treat a condition, a medical professional will often select between treatments based on personal experience rather than data. The desire for better data to select a therapy based on individual patient characteristics is not new. Over the years, it has been called subgroup analytics, comparative effectiveness, tailored therapy, personalized medicine, and precision medicine. The latest name, as advocated by the $21^{st}$ Century Cures Act, is RWE.

The term "real-world evidence" or "RWE" denotes using routinely collected data to provide evidence of clinical outcomes. The collected data may be observational data obtained outside the context of randomized controlled trials (RCTs). The data may be stored in EHRs, medical claims or billing activities databases, registries, patient-generated data, mobile devices, etc. It may be derived from registries.

The EHR as a Data Source for RWE

If the goal is to use data collected during routine care to enable tailored therapy, the EHR must be used. The EHR holds the majority of clinical data collected during routine clinical care.

After a patient visit, the physician writes a detailed narrative of the encounter, may or may not add an item to the structured record such as the problem list, and submits a claim to insurance to be paid. All of this information may be included in the patient's EHR.

The EHR typically includes both structured data and unstructured data. Structured data includes EHR problem, medication, lab, and other coded lists. Unstructured data typically constitutes the majority of EHR content, including physician notes, study reports, and other provider notes such as those from nurses and social workers.

Structured data lists represent a small fraction of data used in routine care and are not intended for clinical studies. It is therefore not surprising that they can result in incorrect clinical assertions. For instance, multiple studies have shown that problem lists are inaccurate and lack granularity. When a doctor records a problem, it is typically true, meaning that precision is close to 100%. However, if a problem exists, the doctor may or may not record it in the problem list, meaning recall (also referred to as "sensitivity," which references whether a condition is documented if a patient has it) may be low in structured data. Multiple peer-reviewed studies have shown that in the problem list, sensitivity often falls below 50% in describing the most important medical conditions, such as cancer and heart attack.

The missingness results in bias. As an example, a study on heart attack treatments demonstrating a 20% difference between study arms would be poorly served by a data set missing 70% of heart attacks and preferentially identifying only the most severe cases (as commonly occurs in problem lists). Increasingly, therefore, there is a desire to go to the heart of clinical documentation, the unstructured narrative used in everyday care which contains 80% of relevant clinical content. But, the unstructured data is recorded as natural language text and is difficult to process, which is one reason that structured data is more commonly used in RWE.

Patient Selection to Create a Study Cohort

Patient selection in RWE studies typically involves defining inclusion and exclusion criteria and identifying patients in a registry or EHR that meet these criteria. The term "phenotype" refers to a set of patient characteristics including problems, findings, meds, labs, and procedures. The phenotype of a patient may be compared against inclusion and exclusion criteria for a study to determine whether the patient is included in or excluded from that study.

Figure 1:
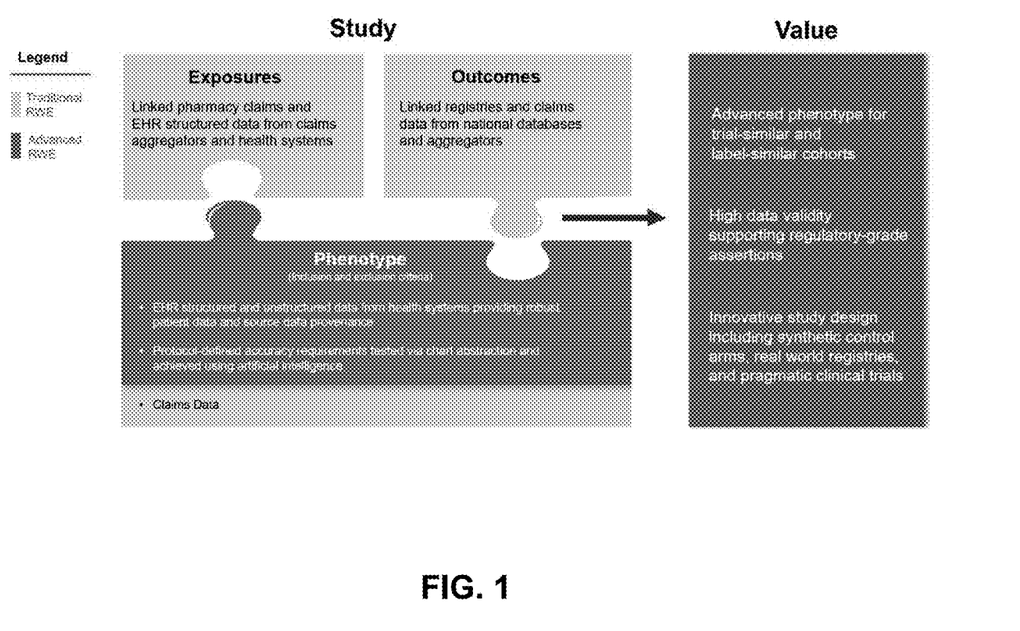
FIG. 1 illustrates a high validity RWE of the present disclosure that incorporates a "deep" phenotype.

As illustrated in FIG. 1, the phenotype represents the foundation of all studies. If the wrong patients are selected for a study, there is little value in assessing exposures and outcomes. For example, if a study is assessing outcomes of patients with diabetes and hypertension but the cohort selected is patients with heart attack and no diabetes, then knowing the outcomes of that cohort is not helpful in determining the outcomes for patients with diabetes and hypertension.

Therefore, before an RWE study can be trusted to influence the standard of care, it should have an acceptable approach to patient selection and proven data validity to ensure the right patients are selected. Required components include data availability, accuracy, and validation. Data availability references whether required data elements exist in the data set. Data accuracy references whether the data element, if it exists, is consistently captured. Data accuracy encompasses recall and precision. Data validation references whether accuracy is measured. This is usually performed by comparing a subset of data against manual chart abstraction acting as a gold standard.

As an example of data availability, it is not possible to study disease-free survival in a claims data set because that outcome is not captured in claims data. In terms of accuracy, it is inadvisable to study smoking in an EHR structured data set because the doctor adds smoking to the problem list for less than 10% of smokers. In terms of validation, it is not safe to study most subgroups in claims or EHR data without validation since these data sets are known to have low recall for granular concepts such as stage 3B colon cancer and systolic heart failure. If half the relevant data in a study are missing, systematic bias can easily lead to erroneous study results.

Data validity, therefore, is a necessary precaution to allow RWE to influence the standard of care. However, current approaches to data validity are insufficiently rigorous to protect patients.

II. Traditional RWE

Patient phenotype is often extracted from claims and other types of EHR structured data. As explained above, recall is often low in such structured data. Key variables may not be available, such as cardiac ejection fraction is not recorded in this data set. More recently, there has been increasing exploration of unstructured records which contain key variables with high accuracy. This led to a proliferation of companies providing RWE in oncology. The approaches undertaken by such companies, however, are flawed.

Traditional RWE is Inherently Inaccurate and Non-Scalable

The RWE approaches employed by modern RWE companies are manual. Each of them has hired an army of annotators to review and annotate unstructured data. They typically use a structured data query to find thousands of patients with a disease out of millions of records. Annotators are then asked to review the thousand records, but not the million.

First, such an approach is limited by the structured data query which is inflexible by definition, and cannot learn from the millions of records.

Second, accuracy is difficult or impossible to measure in traditional RWE. Accuracy is measured as recall and precision. Recall is the proportion of patients correctly identified in each cohort. Precision is the proportion of patients correctly identified divided by the total number of patients identified in each cohort. The F1-score, one measure of accuracy, is the weighted harmonic mean of the precision and recall. In traditional RWE, even though the annotators may confirm that a patient identified using structured data meets criteria (precision), they never see patients that were missed out of millions of records where the structured data element was not included (recall). Therefore, such a traditional RWE approach allows companies to measure precision but is inherently incapable of testing recall. Yet, recall is where most of the error and bias exist.

Third, such a manual approach is highly expensive and not scalable. Within oncology, even though the approach is expensive, high-priced medications make such a high expense acceptable for some studies. However, only the pharmaceutical industry can afford these expensive studies and only for high priority oncology diseases. For many diseases outside of oncology, the level of manual annotation required for large population sizes is entirely infeasible.

III. Advanced RWE

Advanced RWE is More Believable than Traditional RWE

Advanced RWE is defined as high accuracy RWE sufficient to make a clinical assertion. A clinical assertion is a declaration that something has or will happen. For example, a clinical assertion may state that one drug is more effective than another for a subgroup of patients. As another example, a clinical assertion may state that patients with a disease have a specific rate of a specific outcome.

Traditional RWE does not measure accuracy and may be dangerous in making clinical assertions. As a past example, traditional RWE asserted that hormone replacement therapy was useful for post-menopausal women. This led to more than a decade of inappropriate treatment of women with drugs that provided no benefit and caused breast cancer. Inaccurate RWE can lead to incorrect clinical assertions that change behavior of doctors, insurance, and regulators. This behavior, also known as the standard of care, can be changed incorrectly and lead to wrong therapy and patient harm as occurred with hormone replacement therapy.

Advanced RWE assertions are more believable than traditional RWE assertions because advanced RWE is more accurate. The most common source of inaccuracy in RWE is selecting the wrong patient cohort. In RWE, the patient cohort is selected based by matching patient phenotype against inclusion and exclusion criteria for a study. A patient phenotype is a set of characteristics, diseases, symptoms, signs, procedures, medications, laboratory studies, and other clinical and non-clinical information of a patient. If the patient phenotype is inaccurate, the patient may be inappropriately included in or excluded from the study. This can make the clinical assertions wrong. For example, if a study is designed to test whether a drug is useful in diabetes, if an RWE process is used that selects patients who do not have diabetes, it will not matter how accurately the outcomes are measured. That study, if improperly applied to diabetics, would assert that the drug is useful in diabetes where it may actually be harmful in diabetics. This would lead to inappropriate treatment and patient harm.

To solve these and other challenges, advanced RWE uses a deep phenotype and data linkage.

A deep phenotype is a highly accurate phenotype. For example, if EHR structured data was 50% accurate in correctly identifying whether a patient has cancer but EHR unstructured data and data enrichment was 90% accurate, the deep phenotype would require using EHR unstructured data and data enrichment.

Data linkage is connecting multiple data sources for the same patient. For example, for a given patient, the phenotype from EHR unstructured data may be linked to exposure information from EHR structured data. As another example, for a given patient, the phenotype from EHR unstructured and structured data may be linked to the outcome of that patient from a claims data or registry data set.

Advanced RWE is More Scalable than Traditional RWE

At least in this context, the present disclosure provides an advanced approach to RWE that overcomes the problems associated with the traditional RWE. This advanced RWE is able to extract a deep phenotype from rich data sources, using advanced technologies including artificial intelligence. The rich data sources include both unstructured data and structured data from the EHR and may include additional data sources such as claims or registries. The advanced technologies include natural language processing, pattern recognition, inference, and other artificial intelligence approaches. The extraction does not rely on structured data queries which are inflexible and limited in scope. Using rich data sources and advanced technical approaches allows the advanced RWE to retrieve relevant information useful for creating an enriched data set which can be used to achieve a deep phenotype.

Moreover, the present disclosure provides methods for checking the accuracy of the deep phenotype, including its recall, which none of the traditional RWE is capable of measuring. Also, since measurement is possible, the advanced RWE allows an RWE protocol to define a required level of accuracy within a particular study.

Therefore, the deep phenotype can be validated and then used to create a patient cohort that may be linked to exposure or outcome data to make credible clinical assertions. Such advanced RWE based on a validated deep phenotype, accordingly, can be recognized as "research-grade" or "regulatory-grade."

Deep Phenotype

In order to make credible clinical assertions, the RWE needs to be based on accurate extraction of relevant information from the EHR. Structured EHR data simply does not contain all that information, and is far from it. Unstructured data, however, presents an unsurmountable challenge to conventional RWE companies. Language is highly variable in healthcare. A doctor may write "the patient has MA." A study may have an inclusion criterion of migraine with aura. But, "MA" in this context may represent mass or migraine with aura. Conventional RWE companies do not have the technology to handle variable language in millions of records, each of which may have thousands of pages of content.

Association of Concepts

An example of information relevant to the RWE is clinical concepts, or simply concepts. Association of concepts may be useful for extraction of concepts, i.e., identifying concepts from narrative text, and inference of the concepts. Inference of concepts is using additional information to accurately extract a concept.

Associations of concepts may be maintained as a table of associations, which includes pairs or groups of associated concepts. The benefit of building a table of associations is at least three-fold. First, by recognizing related concepts within a narrative, the likelihood that the concept is relevant is increased. Second, when attempting to disambiguate between meanings, relationships may be helpful. Third, when the system is trying to determine which symptom can be explained by a disease, understanding concept relationships can be used to assess each symptom against each disease.

The table of associations does not need to be perfect, as each concept pair is not used in isolation. For example, in a planned application, a single associated concept such as cough will not be sufficient to support pneumonia. Rather, multiple supporting concepts such as a subset of cough, pulmonary infiltrates, gram stain, rales, Zithromax, and fever will be required. Thus, even if a concept pair is incorrectly identified as being related or incorrectly identified as being unrelated, this will not invalidate the system in which most concept pairs are correctly identified as being related or not related.

To build a table of associations, a large corpus of clinical narratives or medical literature may be used. Software reading this content may use co-occurrence, token proximity, or healthcare knowledge databases such as Systematized Nomenclature of Medicine to learn relationships. In this way, for example, it may be learned that migraine, headache, and light sensitivity are related. This learned set of associations may be used in natural language processing or inference algorithms to disambiguate text, to identify a concept as meaningful, or to enable other processing.

Extraction of Clinical Concepts

With the assistance of the table of associations, an advanced RWE approach may start with extraction of concepts. See, e.g., step 202 in FIG. 2 which illustrates an example process of an advanced RWE. Clinical concepts can be extracted from the EHR dataset using artificial intelligence technologies such as natural language processing (NLP), pattern recognition, and inference. Clinical concepts may be problems, medications, procedures, and lab features, without limitation.

Clinical concept extraction is a specialized text extraction which is a process of extracting meaningful concepts from natural language narrative text. Simple text matching can be done with text matching software. A more robust approach, natural language processing, may recognize subject or negations as in "a brother with cancer" or "no hypertension." A more robust approach combines natural language processing with inference as in "Patient with high glucose, uncontrolled DM," where DM can be recognized as diabetes mellitus based on inference from nearby mention of high glucose. A more robust approach combines natural language processing, inference, and pattern recognition as in "Patient with MA. He describes worsening headache and light sensitivity," where the pattern of headache, light sensitivity, and MA is far more likely to be migraine with aura than mass.

Extracted concepts may undergo natural language processing, in some scenarios. Non-limiting examples of cleanup and tagging during natural language processing include removal of special characters, tokenization, sentence splitter, part-of-speech tagger (e.g., tags tokens with part of speech tags such as adjectives, proper nouns), named entity recognition (which matches tokens against an internal map of entities); and negation and subject tagging.

Extracted concepts may undergo inference and pattern recognition, in some scenarios. Context may be used. Context may be as simple as section detection or as complex as reviewing all concepts within a patient narrative.

Section detection helps identify a narrative section to which clinical text can be attributed. This adds context in clinical concept interpretation. For example, a clinical concept appearing in a medical history section may indicate a past condition instead of an ongoing one. Section information is useful in disambiguation of abbreviations and acronyms. For example, the abbreviation CP in a past medical history section may favor cerebral palsy over chest pain depending on other features.

Each clinical note may include two, three or more sections. Without limitation, such sections may be medical history, such as surgical history (e.g., operation dates, operation reports, operation narratives), obstetric history (e.g., pregnancies, any complications, pregnancy outcomes), medications and medical allergies, family history (e.g., immediate family member health status, cause of death, common family diseases), social history (e.g., community support, close relationships, past and current occupation), habits (e.g., smoking, alcohol consumption, exercise, diet, sexual history), immunization records (e.g., vaccinations, immunoglobulin test), developmental history (e.g., growth chart, motor development, cognitive/intellectual development, social-emotional development, language development), demographics (e.g., race, age, religion, occupation, contact information), medical encounters (e.g., hospital admissions, specialist consultations, routine checkups), chief complaint, history of the present illness, physical examination (e.g., vital signs, muscle power, organ system examinations), assessment and plan (e.g., diagnosis, treatment), orders and prescriptions, progress notes, and test results (e.g., imaging results, pathology results, specialized testing).

Context may utilize concepts outside of the sentence boundary and the section header. For example, "Patient with MA. He describes worsening headache and light sensitivity," would require use of information not available to natural language processing since natural language processing ends at the sentence boundary. In this case, a table of associations may be used to understand that headache and light sensitivity are association with migraine with aura but are not associated with mass. Thus, MA may be disambiguated to mean migraine with aura rather than mass.

In some embodiments, along with the concepts, also extracted may be concept attributes. Non-limiting examples of concept attributes include date of occurrence, result, subject, negation, and importance.

Inference of Clinical Concepts

Figure 2:
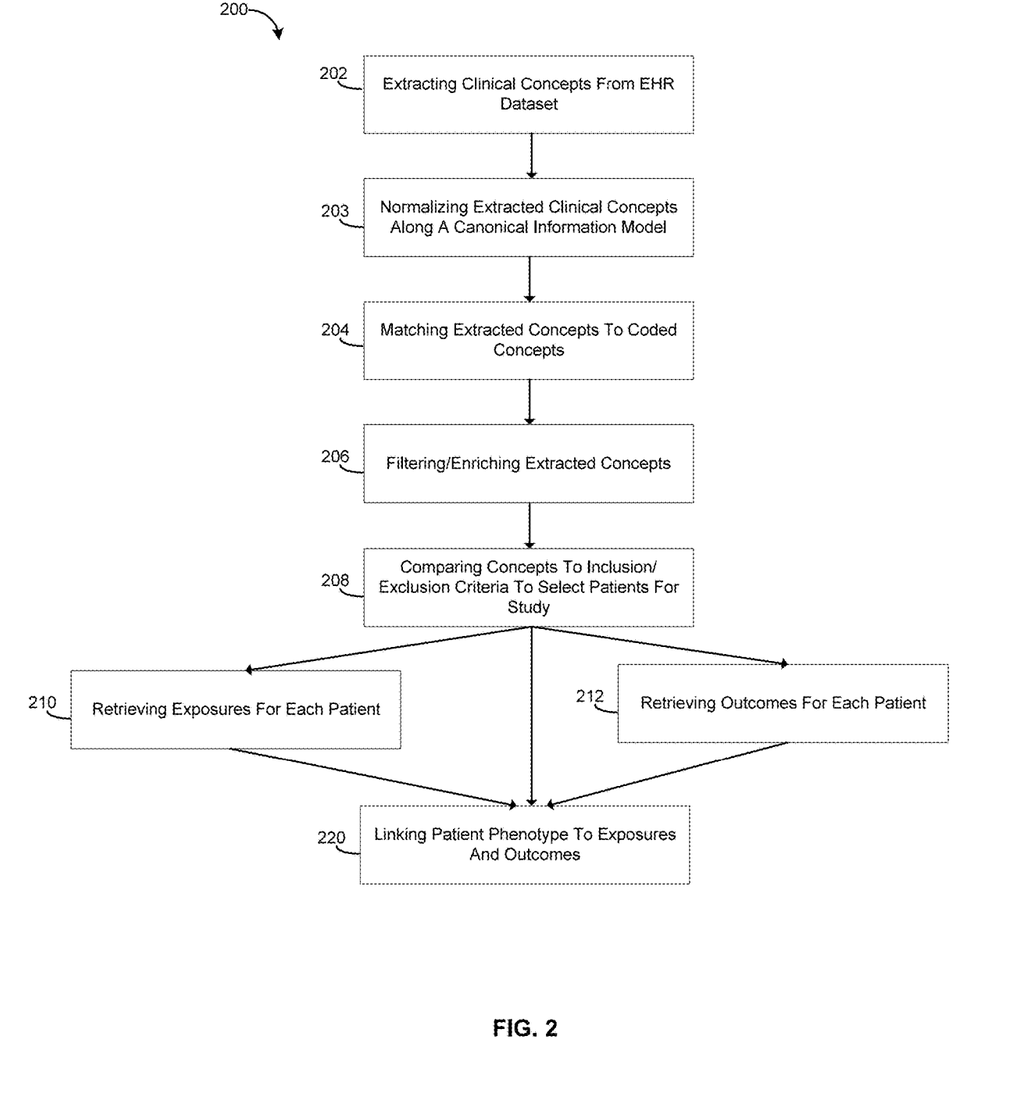
FIG. 2 illustrates an example process of implementing an advanced RWE.

In some instances, the extracted clinical concepts can undergo further filtration and/or enrichment to infer meaning (e.g., step 206 in FIG. 2). Enrichment, e.g., through pattern recognition, can enrich the set of concepts.

In one embodiment, inference may be used to infer which concepts are highly relevant to a given patient's care as would be required to produce a problem list. A problem list is a list of problems for a patient that are current, meaningful, and unique. In one embodiment, the extracted clinical concepts can be assessed against a knowledge database to (1) assess how important an extracted concept is in a patient's care and (2) remove symptoms that can be explained by diseases already identified for the patient. For example, if "the patient has lung cancer and also mentioned unrelated mild elbow pain during the clinic visit," the cancer may be meaningful and the elbow pain may be less important. As another example, if "the patient has a cough and was diagnosed with pneumonia," the pneumonia would be important but the cough is a known symptom of pneumonia and is not as important. Using associations of concepts, meaning and explanation can be inferred. For example, in the patient with cancer, if the entire narrative discusses cancer imaging and cancer therapy but does not mention any associations of elbow pain, it can be inferred that cancer is more important. Thus, using associations can allow software to identify which concepts have more support from related concepts than another. A disease is a single pathophysiologic state that produces signs or symptoms, while a symptom refers to a physical or mental feature that is indicative of a disease.

In some scenarios, each extracted candidate clinical concept may be assessed for being meaningful by testing relationships of other problems, findings, signs, symptoms, procedures, medications, or laboratory studies. For instance, 20-30 problems may exist in a typical 5-7 page history and physical narrative in a typical electronic health record. When a longitudinal record is parsed, however, natural language processing may extract hundreds of potential problems resulting in a clinically meaningless problem list. Similar to problems, a typical patient's electronic health record may include 100+ findings, 2-20 medications, 2-10 procedures, and 5-30 lab values. Thus, an inference module may assess the likelihood that a clinical concept is meaningful by identifying related references within the record.

For example, if two candidate problems are chest pain and pneumonia, first the system will test all discovered features against chest pain. Features within the narrative may include concepts such as EKG (procedure), ST elevation (finding), troponin (lab), coronary artery disease (disease), and aspirin (medication). When compared against the table of associations, there would be five concepts associated with chest pain, resulting in this concept being supported as a strong candidate problem. The system will also assess pneumonia for support. The text may have been "r/o pneumonia" and the natural language processing is not confident whether pneumonia is a real problem. In this task, the concepts of EKG, troponin, coronary artery disease, and aspirin are unassociated with pneumonia as defined by the table of associations. Thus, pneumonia would be considered a less meaningful or low likelihood problem.

To remove symptoms explained by a disease, each symptom in the candidate problem list may be checked against all diseases within the table of associations to assess potential association. A symptom that is related to any disease in the candidate problem list will be discarded.

Concept Coding

The clinical concepts extracted from the EHR dataset, in some scenarios, can then be matched against a listing of coded (or predetermined) clinical concepts (e.g., step 204 of FIG. 2). Such matching is preferably done before concept filtration/enrichment (as shown in FIG. 2), but can also be done afterwards. For instance for a cardiovascular medicine study, the listing of coded clinical concepts may include hyperlipidemia, hypercholesterolemia, coronary artery disease, diabetes mellitus, myocardial infarction, chronic kidney disease, stroke, dementia, cataract, coronary artery bypass graft, atorvastatin, pravastatin, rosuvastatin, simvastatin, LDL cholesterol, HDL cholesterol, and total cholesterol. The list of concepts may be maintained as an industry standard terminology such as Systematized Nomenclature of Medicine (SNOMED), Logical Observation Identifiers Names and Codes (LOINC), International Classification of Diseases (ICD), or RxNorm. In some scenarios, prior to the matching, the extracted clinical concepts may be normalized along a canonical information model (e.g., step 203 of FIG. 2).

Mapping an extracted clinical concept to a coded clinical concept can be done with deterministic or probabilistic techniques, or the combinations thereof. For inexact matches, a probabilistic model can be used to find the most likely matches. Fuzzy matching, in some instances, is performed using approximate dictionary matching.

Validating the Phenotype

Distilling a patient's longitudinal record into a set of coded concepts is creation of a computable phenotype. The phenotype may include demographics, diseases, symptoms, signs, findings, procedures, medications, laboratory studies, and other characteristics. For each coded concept, there may be additional attributes such as date of occurrence, result, subject, negation, and importance.

To run a study on a thousand patients that meet inclusion and exclusion criteria, it may be necessary to test the phenotype of millions of patients. Thus, accurate identification of the phenotype is necessary. An example validation process is illustrated in FIG. 3.

A first step in determining accuracy of the phenotype may be creation of a gold standard for a subset of the patients. For example, if a million patients are analyzed for a cardiovascular study that has 20 inclusion and exclusion criteria, then a subset of this million may be assessed (e.g., step 302 in FIG. 3). The subset may be selected randomly. For example, 5,000 randomly selected longitudinal records may be sampled to determine the accuracy of concept extraction for the million patients.

Figure 3:
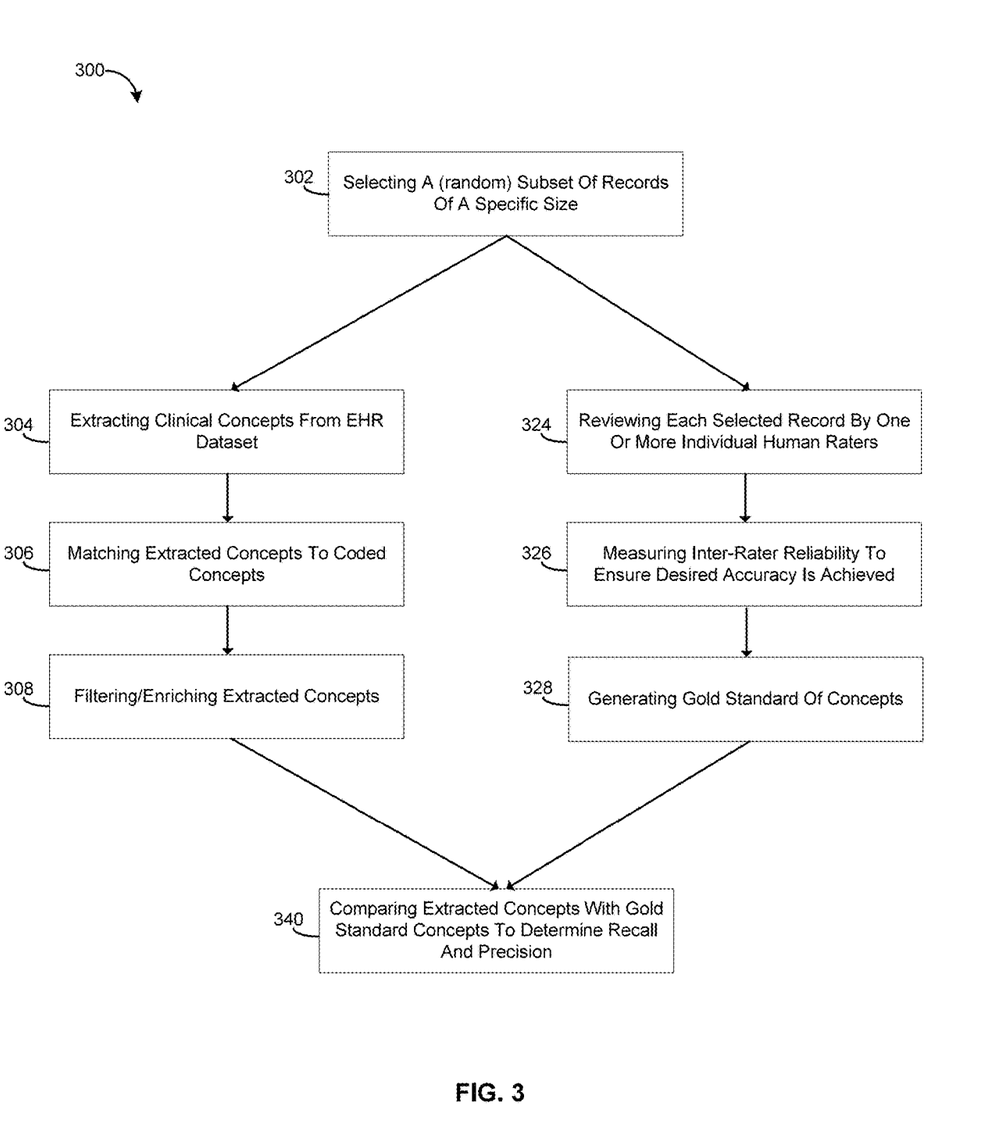
FIG. 3 illustrates an example process of validating a phenotype.

In one embodiment, the gold standard may include a person reviewing each longitudinal record for all or some of the 20 inclusion and exclusion criteria and for additional relevant concepts (e.g., step 324 in FIG. 3). In a preferred embodiment, the gold standard may include two people reviewing each randomly selected record. These annotators may be blinded to each other's annotations and inter-rater reliability may be measured (e.g., step 326 in FIG. 3). In a preferred embodiment, a Cohen's kappa score may be measured and a minimum required kappa score may be required to deem the gold standard sufficiently accurate for use. A gold standard may be considered generated if it meets the minimum requirement (e.g., step 328 in FIG. 3).

For the sampled patient records, automated extraction (e.g., steps 304-308 in FIG. 3 which correspond to steps 202-206 in FIG. 2, respectively) may be compared against the gold standard to determine accuracy of extraction for the sampled patient records (e.g., step 340 in FIG. 3). Accuracy may be measured as recall and precision. Accuracy may be measured as sensitivity and specificity. In a preferred embodiment, a study protocol may require minimum accuracy for a study.

For example, a study that is expecting an effect size of 20% when comparing two treatments may require 80% accuracy of data. In this situation, the study protocol may require a gold standard of at least 1,000 patients with a minimum inter-rater reliability of 0.7. Additionally, the study may require a minimum precision and recall of each inclusion and exclusion criterion of 80%.

Testing the Coded Concepts Against a Study Phenotype

Once the accuracy of extraction has been established and a large corpus of patient records has been turned into an accurate set of coded concepts, these coded concepts may be compared against the study inclusion and exclusion criteria (e.g., step 208 of FIG. 2). Specifically, each patient will have a coded phenotype and the study will have a required coded phenotype. For example, the study phenotype may be patients with age>60 who have diabetes (SNOMED 44054006) but have not had a heart attack (SNOMED 22298006). A patient may have a phenotype of age 64, diabetes (SNOMED 44054006), obesity (SNOMED 414916001), and heart attack (SNOMED 22298006). This patient would not be included in the study because the study excludes heart attack, but the patient has had a heart attack. In this way, a large number of patients may be accurately matched against a very detailed study phenotype.

Linking the Selected Patients to Exposures and Outcomes

Once a set of patients has been identified from the electronic health record for inclusion in the study, it is necessary to understand the exposures and outcomes for each patient. An exposure is an intervention which may influence the course of care. This may be a medication, procedure, or other intervention. An outcome is a result of care. This may be a clinical outcome such as worsening pain, heart attack, or death or may be a financial outcome such as cost of care.

Exposures or outcomes may be available in the EHR. In some circumstances, medication treatments and procedures are tracked in an EHR. In some circumstances, a study may track symptoms or financial claims that are stored in an EHR. In these circumstances, linkage requires only linking different data sets from the EHR.

Often, exposures or outcomes are either not available in the EHR or not complete in the EHR. For example, a patient may be seen in a clinic, but may have some prescriptions filled at an unaffiliated pharmacy. In this situation, some of all medications the patient has received may not be tracked in the EHR and linkage to a pharmacy data set may be required. As another example, if the tracked outcome is heart attack, this may not be tracked in the EHR because the patient may have had a heart attack and be taken to the nearest hospital which has its own EHR system. This may require linkage to claims data since heart attack treatment is billable and a database of claims would track that the patient submitted a claim for heart attack treatment. As another example, if the tracked outcome is death, this may not be tracked in the EHR because the patient may have died at home or a different hospital than where they routinely receive care. This may require linkage to a national death registry.

IV. Computing Systems for Implementing the Advance RWE

Figure 4:
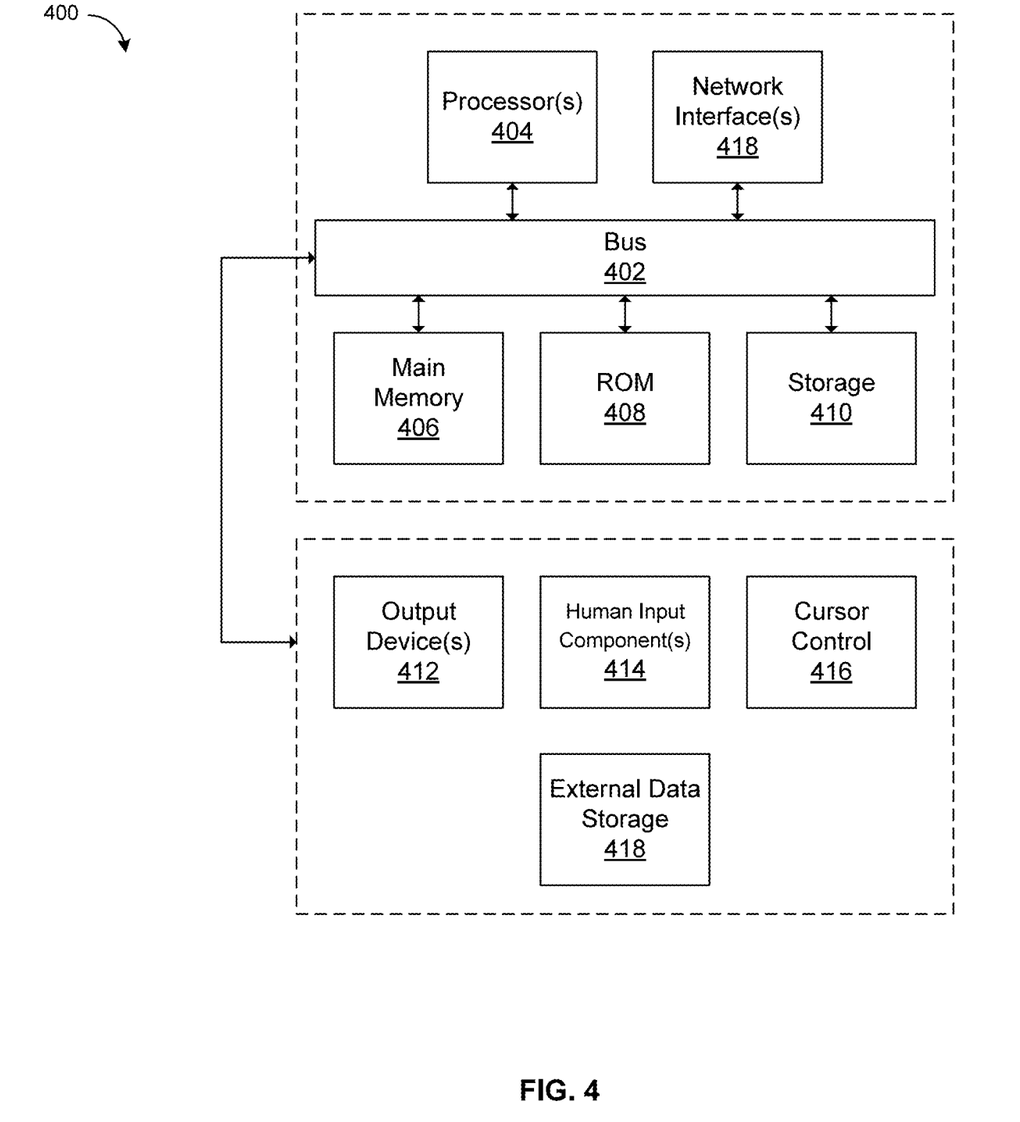
FIG. 4 is a schematic illustrating the computing components that may be used to implement various features of the embodiments described in the present disclosure.

FIG. 4 is a block diagram that illustrates a computer system 400 upon which any embodiments of the advanced RWE and related technologies may be implemented. The computer system 400 includes a bus 402 or other communication mechanism for communicating information, one or more hardware processors 404 coupled with bus 402 for processing information. Hardware processor(s) 404 may be, for example, one or more general purpose microprocessors.

The computer system 400 also includes a main memory 406, such as a random access memory (RAM), cache and/or other dynamic storage devices, coupled to bus 402 for storing information and instructions to be executed by processor 404. Main memory 406 also may be used for storing temporary variables or other intermediate information during execution of instructions to be executed by processor 404. Such instructions, when stored in storage media accessible to processor 404, render computer system 400 into a special-purpose machine that is customized to perform the operations specified in the instructions.

The computer system 400 further includes a read only memory (ROM) 408 or other static storage device coupled to bus 402 for storing static information and instructions for processor 404. A storage device 410, such as a magnetic disk, optical disk, or USB thumb drive (Flash drive), etc., is provided and coupled to bus 402 for storing information and instructions.

The computer system 400 may be coupled via bus 402 to a display 412, such as a LED or LCD display (or touch screen), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. In some embodiments, the same direction information and command selections as cursor control may be implemented via receiving touches on a touch screen without a cursor. Additional data may be retrieved from the external data storage 418.

The computer system 400 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to logic embodied in hardware or firmware, or to a collection of software instructions, possibly having entry and exit points, written in a programming language, such as, for example, Java, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and maybe originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules, but may be represented in hardware or firmware. Generally, the modules described herein refer to logical modules that may be combined with other modules or divided into sub-modules despite their physical organization or storage.

The computer system 400 may implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor(s) 404 executing one or more sequences of one or more instructions contained in main memory 406. Such instructions may be read into main memory 406 from another storage medium, such as storage device 410. Execution of the sequences of instructions contained in main memory 406 causes processor(s) 404 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 410. Volatile media includes dynamic memory, such as main memory 406. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 402. Transmission media can also take the form of acoustic or light waves, such as those generated during radio-wave and infra-red data communications.

Various forms of media may be involved in carrying one or more sequences of one or more instructions to processor 404 for execution. For example, the instructions may initially be carried on a magnetic disk or solid-state drive of a remote computer. The remote computer can load the instructions into its dynamic memory and send the instructions over a telephone line using a component control. A component control local to computer system 400 can receive the data on the telephone line and use an infra-red transmitter to convert the data to an infra-red signal. An infra-red detector can receive the data carried in the infra-red signal and appropriate circuitry can place the data on bus 402. Bus 402 carries the data to main memory 406, from which processor 404 retrieves and executes the instructions. The instructions received by main memory 406 may retrieve and execute the instructions. The instructions received by main memory 406 may optionally be stored on storage device 410 either before or after execution by processor 404.

The computer system 400 also includes a communication interface 418 coupled to bus 402. Communication interface 418 provides a two-way data communication coupling to one or more network links that are connected to one or more local networks. For example, communication interface 418 may be an integrated services digital network (ISDN) card, cable component control, satellite component control, or a component control to provide a data communication connection to a corresponding type of telephone line. As another example, communication interface 418 may be a local area network (LAN) card to provide a data communication connection to a compatible LAN (or WAN component to communicated with a WAN). Wireless links may also be implemented. In any such implementation, communication interface 418 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world-wide packet data communication network now commonly referred to as the "Internet". Local network and Internet both use electrical, electromagnetic or optical signals that carry digital data streams. The signals through the various networks and the signals on network link and through communication interface 418, which carry the digital data to and from computer system 400, are example forms of transmission media.

The computer system 400 can send messages and receive data, including program code, through the network(s), network link and communication interface 418. In the Internet example, a server might transmit a requested code for an application program through the Internet, the ISP, the local network and the communication interface 418.

The received code may be executed by processor 404 as it is received, and/or stored in storage device 410, or other non-volatile storage for later execution. Each of the processes, methods, and algorithms described in the preceding sections may be embodied in, and fully or partially automated by, code modules executed by one or more computer systems or computer processors comprising computer hardware. The processes and algorithms may be implemented partially or wholly in application-specific circuitry.

The various features and processes described above may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the embodiments should, therefore, be construed in accordance with the appended claims and any equivalents thereof.

The various operations of example methods described herein may be performed, at least partially, by one or more processors that are temporarily configured (e.g., by software) or permanently configured to perform the relevant operations. Similarly, the methods described herein may be at least partially processor-implemented, with a particular processor or processors being an example of hardware. For example, at least some of the operations of a method may be performed by one or more processors. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

The performance of certain of the operations may be distributed among the processors, not only residing within a single machine but deployed across a number of machines. In some example embodiments, the processors may be located in a single geographic location (e.g., within a home environment, an office environment, or a server farm). In other example embodiments, the processors may be distributed across a number of geographic locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the subject matter has been described with reference to specific example embodiments, various modifications and changes may be made to these embodiments without departing from the broader scope of embodiments of the present disclosure. Such embodiments of the subject matter may be referred to herein, individually or collectively, by the term "invention" merely for convenience and without intending to voluntarily limit the scope of this application to any single disclosure or concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Although the invention has been described in detail for the purpose of illustration based on what is currently considered to be the most practical and preferred implementations, it is to be understood that such detail is solely for that purpose and that the invention is not limited to the disclosed implementations, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A method for generating a dataset for real-world evidence (RWE), comprising:
constructing a table of association that maintains associations of clinical concepts based on a corpus of clinical narratives or medical literature;
identifying a patient phenotype for a plurality of patients each having a patient record in an electronic health record (EHR) by:
(a) extracting, using an artificial intelligence technology, from the patient record, a plurality of clinical concepts;
(b) determining a level of support for each extracted clinical concept at least based on an association between the extracted clinical concept and other clinical concepts extracted from the same patient record according to the table of association;
(c) identifying, from the plurality of clinical concepts by checking the table of association, a clinical concept representing a symptom already explained by another clinical concept in the plurality of clinical concepts representing a disease;
(d) filtering the extracted clinical concepts by exclusion of (1) extracted clinical concepts having relatively lower levels of support among the extracted clinical concepts, and (2) the clinical concept identified in (c); and
(e) removing at least an extracted concept, thereby obtaining a plurality of clinical concepts representing the patient phenotype for the patient;
identifying a cohort of patients from the EHR with a patient phenotype that satisfies at least a portion of a criteria of a study phenotype;
obtaining, for the cohort, exposure data and outcome data relating to at least a portion of the patients within the identified cohort; and
linking the patient phenotypes to the exposure data or the outcome data to generate a dataset; and
generating a clinical assertion using the dataset for improved care.

2. The method of claim 1, further comprising associating at least a subset of the clinical concepts and concept attributes with a desired phenotype, wherein the desired phenotype satisfies a threshold phenotypic similarity to a phenotype in a randomized controlled trial.

3. The method of claim 1, further comprising associating at least a subset of the clinical concepts and concept attributes with a desired phenotype, wherein the desired phenotype satisfies a threshold phenotypic similarity to a phenotype in an existing or anticipated regulatory- approved label.

4. The method of claim 1, wherein generating the clinical assertion comprises comparing outcomes from the outcome data of the cohort with outcomes from an interventional study so that the cohort functions as a control arm.

5. The method of claim 1, wherein generating the clinical assertion comprises comparing outcomes of the cohort with outcomes from another cohort or another study to determine comparative effectiveness of at least two treatments.

6. The method of claim 1, wherein generating the clinical assertion comprises comparing outcomes of cohorts based on demographically distinct subpopulations on similar treatment regimens to understand heterogeneity of treatment effects on those subpopulations.

7. The method of claim 1, wherein generating the clinical assertion comprises identifying multiple subgroups to determine preferred design of a randomized controlled trial (RCT).

8. The method of claim 1, wherein generating of the clinical assertion comprises implementing the association of the patient phenotype with the exposure data or the outcome data through data linkage with another data set.

9. The method of claim 1, wherein generating the clinical assertion comprises implementing the association of the patient phenotype with the exposure data and the outcome data for the purposes of identifying patient safety events for pharmacovigilance.

10. The method of claim 1, wherein an association between two clinical concepts in the table of association is determined at least by co-occurrence of the two clinical concepts and/or filtered by a proximity threshold between the two clinical concepts in a clinical record.

11. The method of claim 1, wherein the inferring of potential meaning for an extracted clinical concept is at least based on a section from which the clinical concept is extracted.

12. The method of claim 1, wherein the artificial intelligence technology is selected from the group consisting of natural language processing, pattern recognition and inference.

13. The method of claim 1, further comprising validating the cohort.

14. The method of claim 13, wherein the validation comprises:
   creating a manually-generated reference standard for a portion of the clinical concepts within a portion of the patients within the cohort; and
   measuring an accuracy of semantic processing extraction of the clinical concepts for the cohort to determine validity of the cohort with respect to the manually-generated reference standard for a subset of the cohort, based on at least a portion of the inclusion or exclusion criteria.

* * * * *